United States Patent [19]

Fujita

[11] Patent Number: 4,726,354

[45] Date of Patent: Feb. 23, 1988

[54] OSTOMY SKIN BARRIER APPLICATOR

[76] Inventor: Henry K. Fujita, 2062 Costa Ct., Pinole, Calif. 94564

[21] Appl. No.: 21,133

[22] Filed: Mar. 3, 1987

[51] Int. Cl.$^4$ .............................................. A61B 17/00
[52] U.S. Cl. .................................. 128/1 R; 128/303 R; 604/332
[58] Field of Search .................... 128/303 R; 604/332, 604/338

[56] References Cited

U.S. PATENT DOCUMENTS 4,187,850  2/1980  Gust ........................................ 604/54
4,205,678  6/1980  Adair ..................................... 604/343

Primary Examiner—Michael H. Thaler

[57] ABSTRACT

A tool for the ostomate to apply a skin barrier around the stoma. Skin barrier includes washers, flat skin barriers, snap ring wafers and transparent and translucent pouches with skin barriers attached. Opaque pouches may be used but the view in mirror will not be possible.

A minimum of two fingers and thumb of one hand is required to handle the applicator. The skin barrier attaches to the applicator and is not handled. The palm of one hand will firmly attach the skin barrier to the skin.

1 Claim, 5 Drawing Figures

U.S. Patent
Feb. 23, 1988
4,726,354
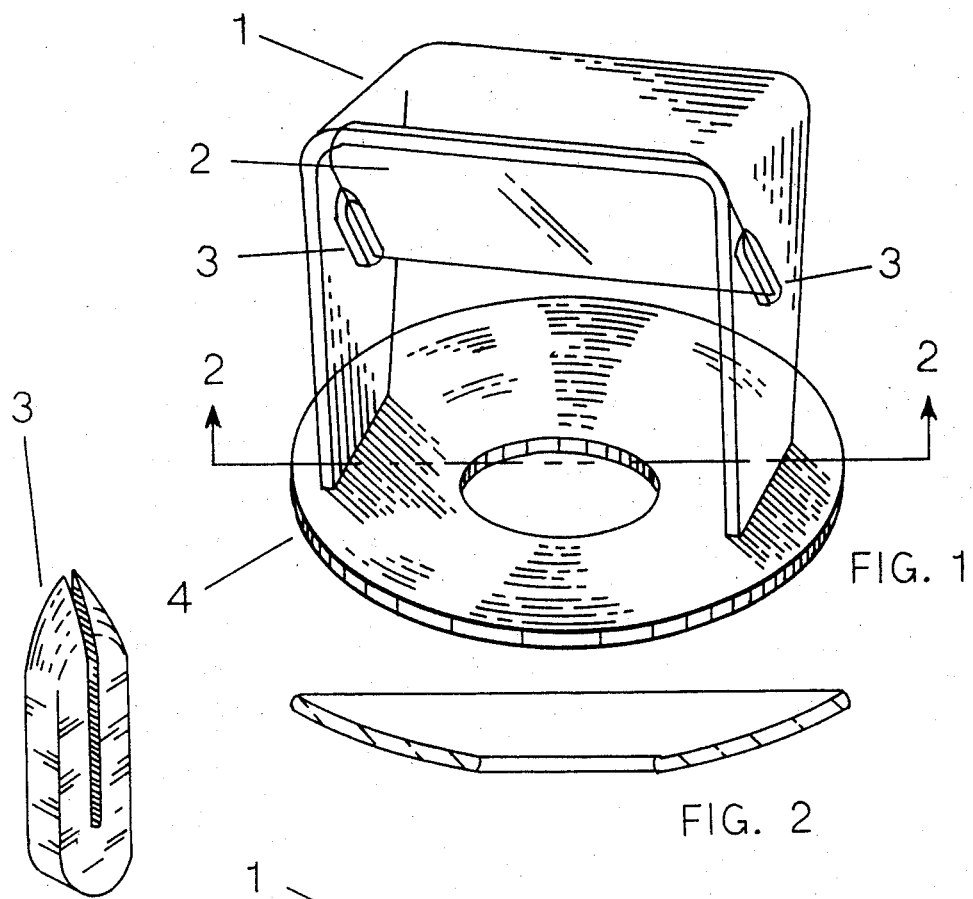
FIG. 1
FIG. 5
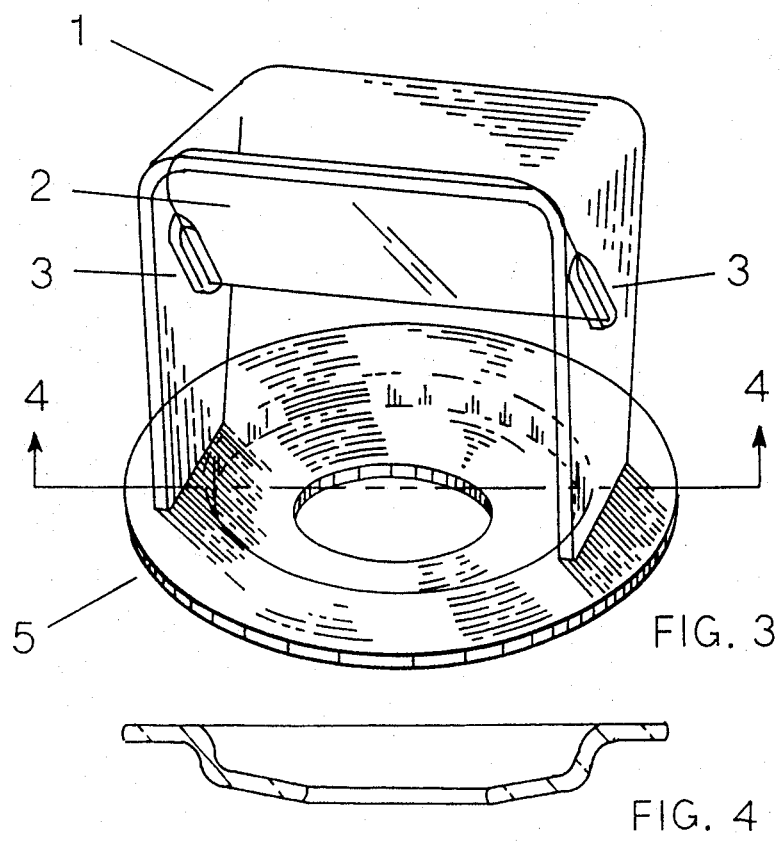
FIG. 2
FIG. 3
FIG. 4

OSTOMY SKIN BARRIER APPLICATOR

BACKGROUND

1. Field of Invention

For the ostomates with an ileostomy, urostomy or a colostomy, this tool holds a skin barrier while it is being positioned over the stoma. It then presses the skin barrier firmly to the skin. The skin barrier can be in any of the varieties commonly used, e.g., washers, plain skin barriers, snap ring wafers or pouches attached to skin barriers.

2. Skin Barrier Application Process

The ostomate uses both hands to handle the skin barrier before and during the stoma locating and application process. The final application is done by pressing down all areas of the barrier with the fingers. Centering the stoma to the barrier was done only from the line of sight view of the ostomate looking down on his abdomen. This gives only a partial view of stoma which must be centered in the hole in the barrier which is approximately 1/16 to ⅛ inch larger than the stoma. This could be a difficult task for those with either a flat or rounded abdomen. Some ostomates use a wall mirror or a small hand mirror to improve vision.

The application of a snap ring wafer presents a more complicated condition. The snap ring is made of hard plastic and stands about 3/16 inch high. Within the ring adjacent to it is a circle of skin barrier approximately ¼ inch wide. The hole within the circle is usually 1/16 to ⅛ inch larger than the stoma which it must encircle. With the skin barrier in place around the stoma, there is a ¼ inch wide circle of skin barrier between the 3/16 inch ring and a normally protruding stoma. Pressing down this depressed area must be done very carefully to avoid injury to the stoma.

I was not able to find any applicating tool similar to the above. My urologist and nurse have never seen anything like this applicator at any new product shows they have attended.

OBJECTS AND ADVANTAGES

Objects and advantages of this applicator are:
1. A full top view of the stoma in a mirror.
2. One hand handling before and during the application. With a skin barrier attached to the applicator, it takes a minimum of two fingers and thumb of either hand to handle, e.g., to pick up or lay down, hold and move it to exact position over the stoma. To press firmly down to the skin takes only the palm of one hand.
3. It is easily cleaned and is resistant to body wastes.
4. The physically and visually handicapped should benefit from the mimimum handling required of this applicator.
5. Can be used anywhere in a standing or prone position.

DESCRIPTION OF DRAWING

FIG. 1 is a perspective view of applicator showing mirror 2 mounted in the handle 1. The mirror 2 is mounted over the hole in base 4 and is angled so the user has a reflected view of the hole. The width across the top surface of handle 1 is slightly wider than the sides.

FIG. 2 is a cross-section of base 4 in FIG. 1 at section line 2—2. This shape is used with washers, flat skin barriers and transparent and translucent pouches. It can be used with opaque pouches by lining up the stoma to the hole in the skin barrier in the usual way and the mirror will not be usable. However, you will still have the ease of handling.

FIG. 3 has the same handle and mirror assembly shown in FIG. 1 but has a base 5 with a different form shown in FIG. 4.

FIG. 4 is a cross-section of base 5 in FIG. 3 at section line 4—4. This form fits inside the ring of a snap ring wafer.

FIG. 5 is a perspective detail view of mirror mount 3 shown in FIGS. 1 and 3 in four places.

DRAWING REFERENCE NUMERALS

1. Handle
2. Mirror
3. Mirror mount
4. Convex base
5. Stepped base

DESCRIPTION OF INVENTION

FIG. 1 shows the applicator with a convex base 4 shown in cross section in FIG. 2. The base 4 is attached to handle 1 of FIG. 1. Handle sides taper slightly wider towards the top. Mirror 2 is attached to handle 1 by mirror mount 3 in two places. FIG. 5 is a perspective view of mirror mount 3. FIG. 3 shows applicator with the same handle as in FIG. 1 but with a base with a different shape shown in cross section in FIG. 4 of section 4—4 of FIG. 3. All corners and end surfaces are rounded and polished for handling safety and sanitation.

Handle is first cemented to their respective bases 4 and 5 with a liquid plastic cememt. A viscous plastic cement is then applied to the 90 degree joints for strength and to make a fairing for easy cleaning and sanitation. The mirror mounts 3 are cemented with liquid plastic cement. The mirror 2 is stainless steel and all edges are rounded and polished. The mirror is mounted at an angle slightly greater than 45 degrees.

Handle 1, base 4 and 5, mirror mount 3 are all made of transparent acrylic plastic 0.090 inch thick minimum. Any other type of easily formed flat plastic stock can be used.

Base 4 was formed over a convex male wood form. Base 5 was formed with male and female wood forms. Handle 1 was formed to a square wood block. All heating for forming was done over a heating element and required only moderate heat.

SKIN BARRIER APPLICATOR

Operation

The applicator of FIG. 1 with the convex base shown in cross section in FIG. 2 can be used with any washer, skin barrier or transparent and translucent pouch attached to a skin barrier. An opaque pouch can be used but it would have to be done without the use of the mirror. While most skin barriers have a self-stick surface, the glue-on types can also be used.

The ostomate uses a base containing a hole slightly larger than his stoma. The skin barrier to be applied in first prepared in the usual manner by trimming, cutting the hole, etc. It is then temporarily taped to the bottom of the base 4 with the holes in the base 4 and the skin barrier lined up and with the mirror 2 facing so that when the skin barrier with applicator attached is placed in the applied position over the stoma, the reflection of the hole in base 4 and the stoma should be seen in the mirror 2. The protective covering on the self-stick surface is left in place until ready to apply.

Taping is simply done by placing the base 4 on top of the skin barrier and running a length of tape straight across the inside surface of the base 4 near the edge with the tape ends running over the edge to the skin barrier. Use two such strips across opposite sides of base 4. Folding over ½ inch on one end of each tape makes it easy to remove after application.

With washers which may be smaller in diameter than the base 4, roll a piece of tape around a finger with the sticky side out. Place two of these loops at opposite edges of the bottom of the base. Line up hole in washer with hole in base 4 and press on. The loop functions as a double sided tape and is easy to remove. Standard masking tape sticks the best but any kind of medical tape may be used with varying degrees of stickiness.

The base 5 shown in FIG. 3 with the cross section of FIG. 4 is used for snap ring wafers. Since these have a narrow circular strip of skin barrier next to and inside the 3/16 inch hard plastic ring, it is difficult as well as time consuming to press down this narrow circular strip. The base 5 with the stepped form presses down this narrow strip with one downward press with the palm of the hand across the top of the handle. The taping of the snap ring wafer is done the same as for base 4. Both bases 4 and 5 have space to place a sponge to absorb bodily discharges, e.g., those with a urostomy who may have a discharge every few seconds.

When ready to make the application, remove the protective covering from the self-stick surface. Holding the applicator by the handle in the most comfortable way, e.g., with both or one hand or a minimum of two fingers and a thumb of one hand. Place the applicator in approximate position over the stoma. Switch concentration to reflected view of stoma in mirror and move applicator to exact position desired. Some ostomates prefer a dead center location while others may prefer a slightly off center location.

When the exact location is found, press down lightly. For the ostomates having regular discharges, place a sponge over the stoma. Now place the palm of one or both hands across the top of the handle and press down firmly. Move the hand in a circular motion so the handle tips in all directions. Repeat the circular motion several times and do it very slowly. Taking your time allows body heat to ensure a good contact between the skin and the skin barrier.

The tape holding the applicator to the skin barrier may be removed before or after making the final firm application. After removal of the applicator, inspect the skin barrier to make sure that all areas are properly attached to the skin.

Some ostomates with no physical of visual handicap may find it just as easy to use the applicator without taping it to the skin barrier. The applicator may be used in a standing or prone position. The mirror attached to the handle allows it to be used anywhere and eliminates the need for a wall mirror and the extra handling required of a hand mirror.

While the above description contains many specificities, the reader should not construe these as limitations on the scope of the invention, but merely as an example of one simple design. Some variations are possible in the shape and design of the base. For example, the bottom of the base could be in the arc of a quarter circle and function like a hand stamp that is rocked back and forth. There could be attaching clips built into the base to eliminate taping.

The handle could be made of flat stock formed round of half round or could be made of solid stock. It could be in the shape of an "L" instead of the inverted "U" and it could have a wide area on top of the handle instead of the narrow strip.

The applicator could be die cast in a one piece unit using a different type of plastic. This offers an opportunity to make still more changes in design.

We claim:

1. An applicating tool holding a skin barrier for placement and firm application of said skin barrier around a stoma comprising:
   (a) a circular base with a protuberance on the bottom surface, said base containing a centered hole,
   (b) a handle above and parallel to plane of said base,
   (c) a reflective surface attached to said handle,
whereby an ostomate is able to:
   (a) apply a skin barrier around the stoma without handling said skin barrier,
   (b) determine precise positioning of said skin barrier from reflected image in mirror,
   (c) press said skin barrier firmly in place with one hand.

* * * * *